United States Patent [19]

Jacquet et al.

[11] 4,324,780
[45] Apr. 13, 1982

[54] COPOLYMERS, PROCESS FOR PREPARING THE SAME AND COSMETIC COMPOSITIONS CONTAINING THE SAME

[75] Inventors: Bernard Jacquet, Antony; Claude Mahieu, Paris; Christos Papantoniou, Montmorency, all of France

[73] Assignee: L'Oreal, Paris, France

[21] Appl. No.: 162,927

[22] Filed: Jun. 25, 1980

Related U.S. Application Data

[62] Division of Ser. No. 897,435, Apr. 18, 1978, Pat. No. 4,237,253.

[30] Foreign Application Priority Data

Apr. 21, 1977 [FR] France ............................. 77 12048
Mar. 14, 1978 [FR] France ............................. 78 07308

[51] Int. Cl.³ .......................... A61K 7/00; A61K 7/06
[52] U.S. Cl. ....................................... 424/47; 424/70
[58] Field of Search .................................. 424/47, 70

[56] References Cited

U.S. PATENT DOCUMENTS 3,990,459 11/1976 Papantoniou ..................... 424/70
4,035,478 7/1977 Mullen ............................. 424/70
4,237,253 12/1980 Jacquet et al. .................... 526/923

*Primary Examiner*—Harry Wong, Jr.

[57] ABSTRACT

A cosmetic composition comprises a cosmetic vehicle and from 0.5–10 percent by weight of at least one copolymer having the formula

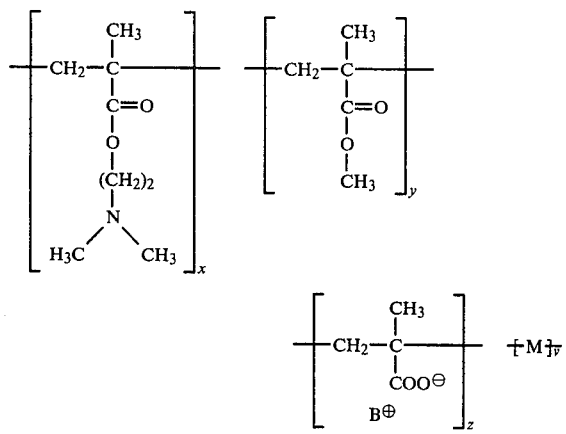

wherein B represents Na, K, $NH_4$,

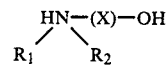

or 2-amino-2-methyl propanol-1; $R_1$ and $R_2$ each independently represent hydrogen or —(X)—OH; X represents alkylene having 1–3 carbon atoms or alkylene substituted by at least one hydroxymethyl; M represents at least one unsaturated monomer selected from acrylamides or methacrylamides substituted on the nitrogen by alkyl, the acrylates or methacrylates of monoalkyl ether of ethylene glycol or of polyethylene glycol, and N-vinylpyrrolidone; x is 22–64 mole percent, y is 13–71 mole percent, z is 6–23 mole percent, v is 0–22 mole percent, and $x+y+z+v$ is equal to 100 mole percent.

7 Claims, No Drawings

COPOLYMERS, PROCESS FOR PREPARING THE SAME AND COSMETIC COMPOSITIONS CONTAINING THE SAME

This is a division of application Ser. No. 897,435, filed Apr. 18, 1978, now U.S. Pat. No. 4,237,253.

The present invention concerns new copolymers, a process of preparing said copolymer, and cosmetic compositions containing them, in particular lacquers and waving lotions.

During recent years numerous synthetic polymers have been proposed for use in compositions for the hair such as lacquers and waving lotions.

In fact, previously used polymers did not give total satisfaction to their (feminine) users because they presented certain disadvantages that limited their regular use.

In particular, either a strong hygroscopicity causing a gluing effect or an unesthetic appearance of the hair or an increased friability of the copolymers entailing the consequent formation of films is experienced on use of said polymers.

The new polymers that have been proposed recently provide remedies for these disadvantages in part, but pose, on the other hand, some problems in formulating the lacquers and waving lotions on account of the lack of solubility of said polymers in certain solvents.

Among the polymers in particular these has been proposed the use of polymers containing functions of quaternized tertiary amines such as those described in the French patent No. 72 32244, polymers resulting from the copolymerization of methyl methacrylate, methacrylate of quaternized dimethylaminoethyl, and octadecyl methacrylate.

Polymers of this type are proven to present a good affinity for hair but they lack brilliance and good mechanical properties. Furthermore, they are not easily compatible with certain propulsive agents used in lacquers.

With the object in part of remedying these various disadvantages and also satisfying users, the synthesis of new copolymers in which at least three constituent monomers have the methacrylic structure has been perfected. In fact, it has been established that these copolymers answer the set of requirements formulated by users and by cosmeticians charged with developing cosmetic compounds such as lacquers and waving lotions.

The copolymers of the invention are indeed endowed with excellent solubility in ethanol and hydroethanolic mixtures; moreover, they exhibit good compatibility with propulsive agents used in the aerosol industry.

Enabled by new industrial products, the present invention has for its purpose some copolymers in which at least three constituent monomers have a methacrylic structure wherein, the copolymers correspond to the following general formula:

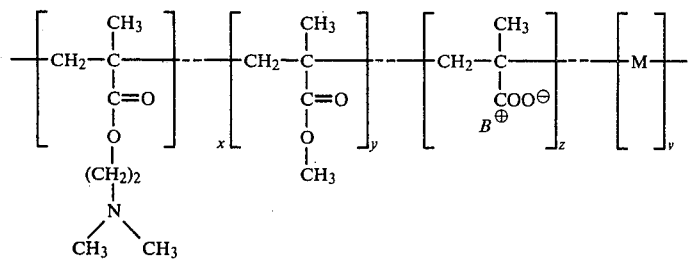

where:

B represents Na, K, NH$_4$, or

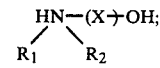

R$_1$ and R$_2$, identical or different, represent an atom of hydrogen or the radical —(X)—OH;

X represents an alkylene radical, branched or unbranched, having from 1 to 3 carbon atoms or an alkylene radical, branched or unbranched, substituted by at least one hydroxymethyl;

M represents at least one typical unsaturated monomer of the group consisting of: the acrylamides or methacrylamides substituted on the nitrogen by an alkyl radical, branched or unbranched, the acrylates or methacrylates of monoalkyl ether of ethylene glycol or of polyethylene glycol, and N-vinyl pyrrolidone;

x is from 22% to 64% in moles;
y is from 13% to 73% in moles;
z is from 6% to 23% in moles; and
v is from 0% to 22% in moles; x+y+z+v being equal to 100%.

According to the invention the acrylamides or methacrylamides substituted on the nitrogen by a branched or unbranched alkyl radical correspond to the following formula:

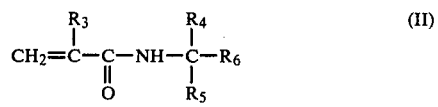

where:

R$_3$, R$_4$, and R$_5$, identical or different, represent either a hydrogen atom or a methyl radical; and R$_6$ is an alkyl radical, branched or unbranched, having from 1 to 11 carbon atoms.

Among the compounds of formula II above one can cite in particular: N-tertiobutyl acrylamide, N-octyl acrylamide, N-decyl acrylamide, N-dodecyl acrylamide, N-(dimethyl-1,1 propyl-1) acrylamide, N-(dimethyl-1,1 butyl-1) acrylamide, N-(dimethyl-1,1 pentyl) acrylamide, as well as the corresponding methacrylamides.

According to the invention, the acrylates or methacrylates of monoalkylether of ethylene or polyethylene glycol correspond to the following formula:

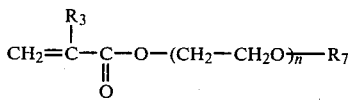

(III)

where:
$R_3$ has the same significance as in formula II;
$R_7$ represents a methyl or ethyl radical; and
n is an integer between 1 and 12.

Among the compounds of formula III one can cite in particular the acrylates and methacrylates of monomethyl or ethyl ether of ethylene or diethylene glycol, and the acrylates and methacrylates of ω-methyl or ethyl polyethylene glycol, and in particular among the latter, the acrylate of formula III in which radical $R_7$ represents a methyl radical and n=7, this acrylate being commercialized by Union Carbide Co. under the trade name of Carbowax-550.

Among the organic or inorganic bases susceptible of leading to embodiments of formula Ia of the copolymer of formula I of the invention, one can cite the following: sodium hydroxide, potassium hydroxide, ammonium hydroxide, and amino-alcohols including monoethanolamine; diethanolamine; triethanolamine; isopropanolamine; diisopropanolamine; tri(hydroxy-2 propyl-1) amine, sold under the trade name of "tri-isopropanolamine" by Ugine-Kuhlman Co.; amino-2 methyl-2 propanol-1; amino-2 methyl-2 propanediol-1,3; and amino-2 hydroxymethyl-2 propanediol-1,3.

Generally, the copolymers of the invention have molecular weights between 10,000 and 1,500,000, and usually between 15,000 and 200,000.

Likewise, an object of the present invention consists of the process of preparation of the new copolymers of the invention.

According to a first embodiment, the copolymers of the invention have been obtained in working out for the first time the copolymerization of a mixture (i) of N,N-dimethylamino-2 ethyl methacrylate, (ii) methyl methacrylate, (iii) methacrylic acid, and (iv) possibly at least one other monomer corresponding to the radical M, and in then neutralizing the free carboxylic acid functions of the copolymer with the aid of an organic or inorganic base chosen among those mentioned above. This procedure is completely suitable particularly when the base is an inorganic base like sodium hydroxide, potassium hydroxide, or ammonium hydroxide.

According to another embodiment, the copolymers of the invention an be obtained by copolymerizing a mixture of (i) N,N-dimethylamino-2 ethyl methacrylate; (ii) methyl methacrylate; (iii) methacrylic acid in its salt form, e.g., reaction with an amino-alcohol of the formula:

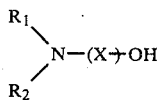

(IV)

where: $R_1$, $R_2$, and X have the same significance as previously; and (iv) possibly at least one other monomer corresponding to the radical M.

Thus this procedure consists first in the preparation of a methacrylate of ammonium with the formula:

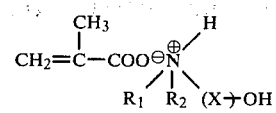

where: $R_1$, $R_2$, and X have the same significance as above through the salt formation of methacrylic acid by an amino-alcohol of formula IV corresponding to the salt required.

This reaction is performed preferably in an organic solvent such as ethyl ether or alcohol at an ambient temperature 0° C. to 20° C.

After obtaining the ammonium salt, the latter is then copolymerized in the presence of other monomers.

Among the different ammonium methacrylates of formula V can be cited in particular; the methacrylate of (hydroxy-1 methyl-2) propyl-2 ammonium, the methacrylate of (dihydroxy-1,3 methyl-2) propyl-2 ammonium, and the methacrylate of tri((hydroxy-2) propyl-1) ammonium.

This process of copolymerization in which the methacrylic acid is made to occur in the salt form is particularly advantageous when one desires to obtain a copolymer no longer containing any free carboxylic acid function.

In fact, according to the second method described above, one cannot be certain of obtaining total neutralization of the set of carboxylic acid functions after the copolymerization, and thus the copolymer obtained can possibly present certain residual odors because of the use as monomer of a portion of the methacrylic acid.

Nevertheless, with the exception of the odor problem, there are not any appreciable differences in the properties of the copolymers obtained from either process.

Whatever process is used for the preparation of the copolymers of the invention, the copolymerization itself is performed with classical methods, i.e., in solution in a solvent, either in mass, or even in suspension in an inert liquid, or in an emulsion. A further procedure includes polymerization by precipitation which consists in using a solvent in which the monomers are soluble but in which the polymers precipitate. According to this process the polymer is isolated by filtration. The solvents appropriate for this type of polymerization include cyclohexane, methylethylketone, heptane, ethyl acetate, etc. The catalysts used are generators of free radicals such as azo-bis-isobutyronitrile, peresters, or oxidation-reduction systems. Among the peresters can be mentioned in particular tertiobutyl ethyl-2 perhexanoate and tertiobutyl perpivalate. Among the oxidation-reduction systems one can cite in particular the aqueous couples of oxygenated ferrous chloride, persulfate of ferrous ammonium chloride, etc.

The quantity of catalyst generally comprises between 0.1% and 6% by total weight of the monomers used for copolymerizing.

In certain cases, copolymerization can likewise be brought about or simply activated by means of irradiation.

The copolymerization reaction is generally performed by heating under nitrogen and agitation at a temperature about 55° C. to 85° C.

The duration of heating is preferably between 6 and 24 hours.

When according to the invention one uses the process consisting of preparing first an ammonium methacrylate of formula V, after its formation the latter is not isolated, but is immediately copolymerized with other monomers in the reaction medium having served in its preparation.

In the latter case the solvent is preferably an alcohol, and especially ethanol.

The present invention similarly has for its object, new industrial products based on a cosmetic composition containing from 0.5% to 10% by weight at least of a copolymer of formula I and in the form of a lacquer or a waving lotion, or again in the form of a shampoo, a tint, or of a treatment lotion applied before or after shampooing or tintint.

Waving lotions of the invention present themselves in the form of aqueous or hydroalcoholic solutions containing from 20% to 70% alcohol and have a concentration of copolymer comprising between 1% and 3% by weight.

The alcohols generally used for such waving lotions are preferably lower aliphatic alcohols of low molecular weight, such as ethanol or isopropanol.

These waving lotions can in addition contain diverse adjuncts such as plastifiers, perfumes, and colorings.

The lacquers for the hair of the invention are obtained by placing in solution in an alcohol at least one copolymer as defined previously, this solution being placed in an aerosol bomb and mixed with a propellant agent.

According to this form of embodiment, the copolymer is generally present in a proportion comprising between 0.5% and 10% by weight.

The lacquers likewise can contain a third-part solvent that can be present in a proportion between 3% and 35% by weight.

The alcohol, which can be either ethanol or isopropanol, generally is present in a proportion between 5% and 80%, and preferably between 6% and 69.5% by weight.

Among the third-part solvents that can be used in the lacquers one can cite in particular methylene chloride, trichloroethane, ethyl chloride, acetone, ethyl acetate, and dichlorodifluoroethane.

As propellant agents one can use fluorochloric hydrocarbons either alone or in a mixture such as that known under the trade name of Freon; in particular, Freon 11, 12, 22, and 142b. Similarly, one can use as propellant agent carbon dioxide or nitrous oxide, or hydrocarbons such as propane, butane, isobutane, etc., these propellent being used either alone or mixed together, or with one or several Freon mixtures such as those mentioned above. According to a preferred embodiment, the Freons are employed in combination with carbon dioxide or nitrous oxide.

According to a variant of the invention, the copolymers of formula I similarly can be used in compositions of the invention in association with other polymers of anionic or cationic character, the compositions appearing then in the form of creams, gels, emulsions, etc.

In this embodiment the polymer with anionic or cationic character is present in the composition at a concentration between 0.01% and 10%, and preferably between 0.02% and 5%.

The compositions of the invention can contain, or course, in addition, other ingredients such as those generally used in cosmetics, such as plastifiers, brilliantines, perfumes, colorings, restructuring agents, and some anionic, cationic, or non-ionic massaging agents.

Finally, the present invention has for its object a process for waving hair. According to this procedure, one applies on the hair at least one waving lotion such as described above before rolling the hair on waving rollers (of diameter 15 to 30 mm), and one then submits the hair to drying (at temperatures of the order of 25° C. to 55° C.).

The amount applied to the hair depends on the volume of the head, but is generally of the order of 10 to 100 cm$^3$, and preferably of the order of 20 to 50 cm$^3$.

Finally, to improve the understanding of the invention, several examples of preparation of the copolymers of the invention as well as several non-limiting examples of cosmetic compositions based on these copolymers will now be described.

EXAMPLES

Example I (a) Preparation of methacrylate of (hydroxy-1 methyl-2) propyl-2 ammonium.

In a round-bottom flask of 250 ml provided with a refrigerant and mechanical agitation, one introduces 50 g of ethyl ether and 10 g (0.112 moles) of amino-2 methyl-2 propanol-1. The solution is refrigerated at 0° C. in an ice bath until the stoichiometric quantity of methacrylic acid (9.65 g) to neutralize completely the amino alcohol is introduced under vigorous agitation. The methacrylate of (hydroxy-1 methyl-2) propyl-2 ammonium precipitates in the form of a white powder that is filtered and dried at 20° C. under reduced pressure. Yield: 100%.

According to the same mode of operation described above, one has similarly prepared, starting with amino-2 methyl-2 propanediol-1,3, the methacrylate of (dihydroxy-1,3 methyl-2) propyl-2 ammonium, and beginning with "tri-isopropanolamine," the methacrylate of tri((hydroxy-2) propyl-1) ammonium.

(b) Preparation of the copolymer of N,N-dimethylamino-2 ethyl methacrylate (38%), methyl methacrylate (48%), and (hydroxy-1 methyl-2) propyl-2 ammonium methacrylate (14%) (in moles).

In a 1-liter reactor provided with a refrigerant, mechanical agitation, and a nitrogen inflow, one introduces 60 g of absolute ethanol, 36.2 g (0.362 mole) of methyl methacrylate, 45.3 g (0.288 mole) of N,N-dimethylamino-2 ethyl methacrylate, 18.5 g (0.106 mole) of (hydroxy-1 methyl-2)propyl-2 ammonium methacrylate, and 1 g of azo-bis-isobutyronitrile in solution in 100 g of absolute ethanol. The reaction mixture is then heated at 75° C. under agitation for 8 hours. The polymer obtained with a quantitative yield is soluble in absolute ethanol. Viscosity: 1.96 cp in 5% solution in dimethylformamide at 34.6° C.

Example II

Preparation of the copolymer of N,N-dimethylamino-2 ethyl methacrylate (48%), methyl methacrylate (41%), and (hydroxy-1 methyl-2) propyl-2 ammonium methacrylate (11%) (in moles).

As in example Ib described above, one similarly has copolymerized 30 g (0.3 mole) of methyl methacrylate, 55 g (0.35 mole) of N,N-dimethylamino-2 ethyl methacrylate, and 15 g (0.086 mole) of (hydroxy-1 methyl-2) propyl-2 -ammonium methacrylate.

The polymer obtained presents a viscosity of 1.90 cp in 5% solution in DMF at 34.6° C.

Example III

Preparation of the copolymer of N,N-dimethylamino ethyl methacrylate (56%), methyl methacrylate (29%), (hydroxy-1 methyl-2) propyl-2 -ammonium methacrylate (15%) (in moles).

This polymer similarly has been obtained according to the procedure described in example Ib above by preceeding with the copolymerization of: 20 g (0.2 mole) of methyl methacrylate, 62 g (0.395 mole) of N,N-dimethylamino-2 ethyl methacrylate, and 18 g (0.103 mole) of (hydroxy-1 methyl-2) propyl-2 ammonium methacrylate.

The copolymer obtained shows a viscosity of 2.00 cp in 5% solution in DMF at 34.6° C.

Example IV

Preparation of the copolymer of N,N-dimethylamino-2 ethyl methacrylate (31.5%), methyl methacrylate (41%), (hydroxy-1 methyl-2) propyl-2 ammonium methacrylate (17%), and N-tertiobutylacrylamide (10.5%) (in moles).

In a round-bottom flask provided with a refrigerant, mechanical agitation, and nitrogen inflow, one introduces 37 g of N,N-dimethylamino-2 ethyl methacrylate, 30.5 g of methyl methacrylate, 22.5 g of (hydroxy-1 methyl-2) propyl-2 ammonium methacrylate, 10 g of N-tertiobutyl acrylamide, and 0.4 g of azo-bis-isobutyronitrile in solution in 125 g of absolute ethanol. The reaction mixture is then heated under agitation at 78° C. for about 8 hours.

The copolymer obtained is soluble in absolute ethanol. Viscosity: 2.35 cp in 5% solution in DMF at 35.6° C.

Example V

Preparation of the copolymer of N,N-dimethylamino-2 ethyl methacrylate (30%), methyl methacrylate (35%), (hydroxy-1 methyl-2) propyl-2 ammonium methacrylate (14%), and N-pyrrolidone (21%) (in moles).

According to example IV described above, one similarly copolymerizes 27 g of methyl methacrylate, 36.5 g of N,N-dimethylamino-2 ethyl methacrylate, 18.5 g of (hydroxy-1 methyl-2) propyl-2 ammonium methacrylate, and 18 g of N-vinylpyrrolidone in the presence of 1 g of azo-bis-isobutyronitrile in 100 g of absolute ethanol.

The polymer obtained shows a viscosity of 2.07 cp in 5% solution in dimethylformamide (DMF) at 34.6° C.

Example VI

In this example one describes the preparation of a copolymer of the invention by the process consisting of a first period of preparing the polymer in free-acid form, and of a second period of neutralizing the carboxylic acid functions by an organic or inorganic base.

(a) Preparation of the copolymer of N,N-dimethylamino-2 ethyl methacrylate (38.6%), methyl methacrylate (42.5%), methacrylic acid (14.4%), and N-tertiobutyl acrylamide (4.8%) (in moles).

In a 1-liter round-bottom flask provided with a refrigerant, mechanical agitation, and nitrogen inflow, one introduces 50 g of N,N-dimethylamino-2 ethyl methacrylate, 35 g of methyl methacrylate, 10 g of methacrylic acid, 5 g of N-tertiobutylacrylamide, and 1 g of azo-bis-isobutyronitrile in solution in 200 g of absolute ethanol. The reaction mixture finally is heated at 75° C. under agitation for 8 hours.

The copolymer is obtained with a quantitative yield. Viscosity: 2.02 cp in 5% solution in DMF at 34.6° C.

(b) The copolymer obtained according to example VIa above, after having been placed in solution in ethanol, is neutralized with the stoichiometric quantity of amino-2 methyl-2 propanol-1.

The copolymer thus obtained shows a viscosity of 1.78 cp in 5% solution in dimethylformamide at 34.6° C.

The copolymer obtained according to this example can be used directly in ethanol solution for the embodiment of cosmetic compositions using this solvent as medium.

Examples VII to XXI

According to the same operating mode as that described above in examples VIa and VIb, one similarly prepares the copolymers of the invention assembled into table I following.

TABLE I

| EXAMPLE | VII | VIII | IX | X | XI | XII | XIII | XIV | XV | XVI | XVII | XVIII | XIX | XX | XXI |
|---|---|---|---|---|---|---|---|---|---|---|---|---|---|---|---|
| Methacrylate of N,N-dimethylamino-2 ethyl | 50 | 59 | 55 | 60 | 50 | 42 | 35 | 42 | 42 | 45 | 42 | 42 | 42 | 33,5 | 40 |
| Methacrylate of methyl | 40 | 33 | 35 | 30 | 25 | 33 | 40 | 36 | 34 | 25 | 39 | 34 | 42 | 44,5 | 31 |
| Methacrylic acid | 10 | 8 | 10 | 10 | 10 | 10 | 10 | 12 | 12 | 15 | 14 | 12 | 10,7 | 11 | 10 |
| N-tertiobutyl acrylamide | | | | | 15 | 15 | 15 | 10 | 12 | 15 | 5 | 12 | | | |
| Acrylate of formula III in which: $R_3 = H$, $R_7 = CH_3$ and $n = 12$ | | | | | | | | | | | | | 5,3 | 11 | |
| N-vinylpyrrolidone | | | | | | | | | | | | | | | 19 |
| Azo bis-isobutyronitrile (catalyst) | 1 | 1 | 1 | 1 | 0,7 | 0,6 | 1 | 0,5 | 0,4 | 0,4 | 0,4 | 0,2 | 1 | 1 | 1 |
| Viscosity of the copolymer | 2,38 | 2,5 | 2,25 | 2,30 | 2,27 | 2,45 | 2,70 | 2,48 | 2,63 | 4,05 | 2,38 | 3,80 | 2,42 | 2,48 | 3,09 |
| Acid index | 64,4 | 65,9 | 66 | 64 | 58,3 | 63,8 | 63,3 | 70,4 | 70,8 | 83,0 | 80,5 | 70,0 | 65,5 | 66,1 | 65,9 |
| Ethanol | 200 | 200 | 200 | 200 | 100 | 100 | 100 | 150 | 150 | 100 | 150 | 100 | 100 | 100 | 100 |
| Amino alcohol (sufficient quantity required for neutralization) | a | a | a | a | a | a | a | a | a | a | a | a | a | a | a |
| Viscosity of the copolymer neutralized | 1,78 | 1,95 | 1,85 | 2,00 | 2,15 | 2,52 | 2,65 | 2,41 | 2,51 | 3,82 | 2,44 | 3,72 | 2,45 | 2,36 | 2,85 |

Footnotes:
a = amino-2 methyl-2 propanol-1
The quantities of the monomers, of the catalyst, and of ethanol are expressed by weight. The duration of the polymerization is about 8 hours.
Viscosity was measured in 5% solution in dimethylformamide at 34,6°, and values are expressed in centipoise (cp).

EXAMPLES OF COMPOSITIONS

Example 1

One prepares according to the invention an aerosol lacquer by mixing the following ingredients:

| Polymer obtained according to example I | 6.5 g |
|---|---|
| Perfume | 0.2 g |
| Ethanol (sufficient quantity) | 100 g |

25 g of this composition are packaged in an aerosol bomb with 45 g of trichlorotrifluoromethane and 30 g of dichlorodifluoromethane.

Example 2

One prepares according to the invention a waving lotion by mixing the following ingredients:

| Polymer obtained according to example III | 2 g |
|---|---|
| Perfume | 0.1 g |
| Ethanol | 45 g |
| Water (sufficient quantity) | 100 g |

Example 3

One prepares according to the invention a waving lotion by mixing the following ingredients:

| Copolymer obtained according to example IV | 2 g |
|---|---|
| Perfume | 0.1 g |
| Ethanol | 45 g |
| Water (sufficient quantity) | 100 g |

Example 4

One prepares according to the invention an aerosol lacquer by mixing the following ingredients:

| Copolymer obtained according to example V | 6.5 g |
|---|---|
| Perfume | 0.2 g |
| Ethanol (sufficient quantity) | 100 g |

25 g of this composition are packaged in an aerosol bomb with 45 g of trichlorotrifluoromethane (Freon-11) and 30 g of dichlorodifluoromethane (Freon-12).

Example 5

One prepares according to the invention an aerosol lacquer by mixing the following ingredients:

| Copolymer obtained from example XVIII | 2 g |
|---|---|
| Perfume | 0.06 g |
| Ethanol | 38 g |
| Freon-142b | 10 g |
| Carbon dioxide gas (sufficient quantity) | 8 bars |

Example 6

One prepares according to the invention an aerosol lacquer by packaging in a bomb the following ingredients:

| Copolymer prepared according to example XI | 2 g |
|---|---|
| Ethanol | 42 g |
| Methylene chloride | 20 g |
| Propellant (35% propane, 65% butane, sufficient quantity) | 3.2 Kg |

Example 7

One prepares according to the invention an aerosol lacquer by conditioning in a bomb the following ingredients:

| Copolymer obtained according to example XIV | 2 g |
|---|---|
| Ethanol | 42 g |
| Methylene chloride | 35 g |
| Propellant agents: 35% propane, 65% butane, (sufficient quantity) | 3.2 Kg |

Example 8

One prepares according to the invention an aerosol lacquer packaged in a bomb with the following ingredients:

| Copolymer obtained according to example XVIII | 2 g |
|---|---|
| Ethanol | 25 g |
| Methylene chloride | 35 g |
| Propellant agent: 35% propane, 65% butane (sufficient quantity) | 3.2 Kg |

Example 9

One prepares according to the invention an aerosol lacquer by mixing the following ingredients:

| Copolymer obtained according to example XVIII, but neutralized with tri-isopropanolamine | 8.8 g |
|---|---|
| Plastifier ("Fluid 2 C-190" sold by Dow Corning Co.) | 0.16 g |
| Methylene chloride | 60 g |
| Ethanol (sufficient quantity) | 100 g |

25 g of this composition are packaged in an aerosol bomb with 75 g of a mixture of 50% Freon-11 and 50% Freon-12.

Example 10

One prepares according to the invention an aerosol lacquer by mixing the following ingredients:

| Copolymer obtained according to example XIV | 7.6 g |
|---|---|
| Plastifier (Rhodorsil 70.633 V 30, sold by the Rhone-Poulenc Co. | 0.2 g |
| Ethanol (sufficient quantity) | 100 g |

22 g of this composition are packaged in an aerosol bomb with 78 g of a mixture of 61.5% Freon-11 and 38.5% Freon-12.

Example 11

One prepares according to the invention an aerosol lacquer by mixing the following ingredients:

| Copolymer obtained according to example XVIII | 5.2 g |
|---|---|
| Plastifier (Solulan 16, sold by the Amerchol Co.) | 0.25 g |
| Ethanol (sufficient quantity) | 100 g |

30 g of this composition are packaged in an aerosol bomb with 70 g of a mixture of 50% Freon-11 and 50% Freon-12.

Example 12

One prepares according to the invention an aerosol lacquer by packaging in a bomb the following ingredients:

| Copolymer obtained according to example XIV | 2.5 g |
|---|---|
| Ethanol | 50 g |
| Methylene chloride | 20 g |
| Propellant agent: 35% propane, 65% butane | 30 g |

Example 13

One prepares according to the invention a shampoo by mixing the following ingredients:

| Copolymer obtained according to example VII, neutralized with sodium hydroxide | 0.103 g |
|---|---|
| Polymer prepared according to example Xb of French patent No. 77 06031 | 0.897 g |
| Triethanolamine laurysulfate | 10 g |
| Water (sufficient quantity) | 100 g |

The shampoo is left in contact with the hair for 15 minutes before rinsing, making the hair bright and soft to the touch.

Example 14

One prepares according to the invention a shampoo by mixing the following ingredients:

| Copolymer obtained according to example XV, neutralized with sodium hydroxide | 0.6 g |
|---|---|
| Resin Gantrez-ES 425, sold by the General Anilin Film Corp., neutralized with sodium hydroxide | 0.4 g |
| A compound of formula: C$_{9-12}$—CH(OH)—CH$_2$—O(CH$_2$—CH(OH)—CH$_2$—O)$_{3.5}$H$_5$ | 10 g |
| Hydrochloric acid (sufficient quantity) pH = 7 | |
| Water (sufficient quantity) | 100 g |

One applies the shampoo obtained above for 15 minutes before rinsing the hair, which is bright and soft to the touch.

Example 15

One prepares according to the invention the following shampoo by mixing the following ingredients:

| Copolymer prepared according to example XV, neutralized with sodium hydroxide | 0.5 g |
|---|---|
| Polymer of methacrylic acid, sold by Allied Colloids Corp. under the trade name Versicol-K11, neutralized with sodium hydroxide | 0.3 g |
| A compound of the formula: C$_{9-12}$—CH(OH)—CH$_2$—O(CH$_2$—CH(OH)—CH$_2$—O)$_{3.5}$H$_5$ | 10 g |
| Hydrochloric acid (sufficient quantity) pH = 7 to 9 | |
| Water (sufficient quantity) | 100 g |

We claim:

1. A cosmetic composition comprising in an appropriate cosmetic vehicle from 0.5–10 percent by weight of at least one copolymer having the formula

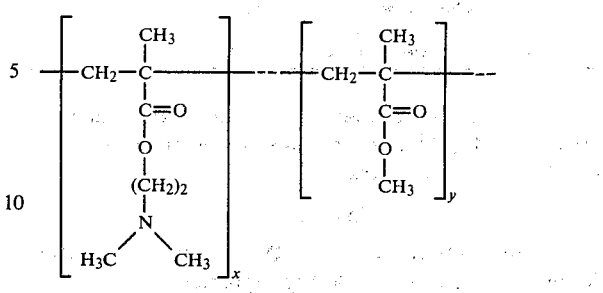

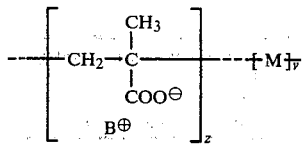

wherein

B represents Na, K, NH$_4$,

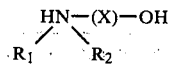

or 2-amino-2-methyl propanol-1;

R$_1$ and R$_2$ each independently represent hydrogen or —X—OH;

X represents alkylene having 1–3 carbon atoms or alkylene substituted by at least one hydroxymethyl;

M represents at least one unsaturated monomer selected from the group consisting of acrylamide substituted on the nitrogen by alkyl, methacrylamide, substituted on the nitrogen by alkyl, acrylate or monoalkyl ether of ethylene glycol, acrylate of monoalkyl ether of polyethylene glycol, methacrylate of monoalkyl ether of ethylene glycol, methacrylate of monoalkyl ether of polyethylene glycol and N-vinyl pyrrolidone;

x is 22–64 mole percent;

y is 13–17 mole percent;

z is 6–23 mole percent;

v is 0–22 mole percent; and x+y+z+v is equal to 100 mole percent.

2. The cosmetic composition of claim 1 wherein said cosmetic vehicle is water or a hydroalcoholic solution where the alcohol moiety thereof ranges from 20–70 weight percent, and wherein said copolymer is present in an amount ranging from 1 to 3 weight percent of said composition.

3. The cosmetic composition of claim 1 which includes another polymer having anionic or cationic characteristics in an amount between 0.01 and 10 percent by weight of said composition.

4. A cosmetic composition for the hair comprising in an appropriate cosmetic vehicle an effective amount of at least one copolymer having the formula

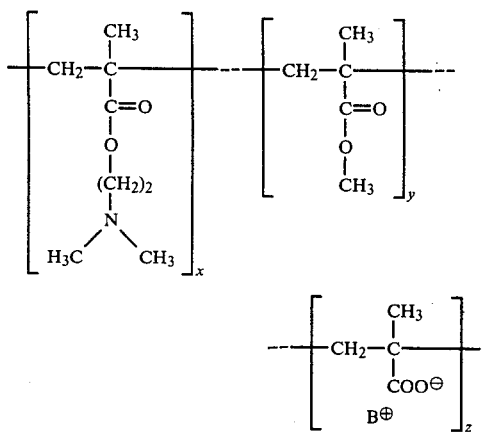

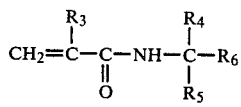

wherein
B represents Na, K, NH$_4$,

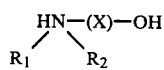

or 2-amino-2-methyl propanol-1;
R$_1$ and R$_2$ each independently represent hydrogen or —X—OH;
X represents alkylene having 1-3 carbon atoms or alkylene substituted by at least one hydroxymethyl;
M represents at least one unsaturated monomer selected from the group consisting of
(1) a monomer having the formula

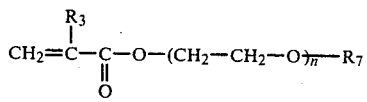

wherein R$_3$, R$_4$ and R$_5$ each independently represent hydrogen or methyl and R$_6$ is alkyl having 1-11 carbon atoms;
(2) a monomer of the formula

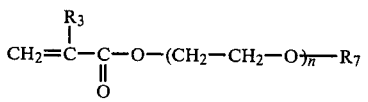

wherein R$_3$ is hydrogen or methyl, R$_7$ is methyl or ethyl and n is an integer from 1-12; and (3) N-vinylpyrrolidone;
x is 22-64 mole percent;
y is 13-71 mole percent;
z is 6-23 mole percent;
v is 0-22 mole percent; and
x+y+z+v is equal to 100 mole percent.
5. The cosmetic composition of claim 4 wherein said copolymer is present in an amount ranging from 0.5-10 percent by weight of said composition.
6. The cosmetic composition of claim 4 wherein said copolymer has a molecular weight ranging from 10,000 to 1,500,000.
7. A cosmetic composition for the hair comprising in a cosmetic vehicle selected from an alcohol and an aqueous alcoholic solution an effective amount of a copolymer selected from the group consisting of
(1) a copolymer of N,N-dimethylamino-2-ethyl methacrylate, methyl methacrylate and (1-hydroxy-2-methyl) 2-propyl ammonium methacrylate;
(2) a copolymer of N,N-dimethylamino-2-ethyl methacrylate, methyl methacrylate, (1-hydroxy-2-methyl) 2-propyl ammonium methacrylate and N-tert.butyl acrylamide;
(3) a copolymer of N,N-dimethylamino-2-ethyl methacrylate, methyl methacrylate, (1-hydroxy-2-methyl) 2-propyl ammonium methacrylate and N-vinylpyrrolidone;
(4) a copolymer of N,N-dimethylamino-2-ethyl methacrylate, methyl methacrylate, methacrylic acid and N-tert.butyl acrylamide, said copolymer being neutralized with 2-amino-2-methyl propanol-1;
(5) a copolymer of N,N-dimethylamino-2-ethyl methacrylate, methyl methacrylate and methacrylic acid, said copolymer being neutralized with 2-amino-2-methyl-propanol-1;
(6) a copolymer of N,N-dimethylamino-2-ethyl methacrylate, methyl methacrylate, methacrylic acid and an acrylate of the formula $$CH_2=\overset{R_3}{\underset{}{C}}-\underset{\overset{\|}{O}}{C}-O-(CH_2-CH_2-O)_{\overline{n}}-R_7$$

wherein R$_3$ is hydrogen, R$_7$ is CH$_3$ and n is 12, said copolymer being neutralized with 2-amino-2-methyl propanol-1; and
(7) a copolymer of N,N-dimethylamino-2-ethyl methacrylate, methyl methacrylate, methacrylic acid and N-vinylpyrrolidone, said copolymer being neutralized with 2-amino-2-methyl propanol-1.

* * * * *